(12) United States Patent
Niitsuma

(10) Patent No.: US 8,187,216 B2
(45) Date of Patent: May 29, 2012

(54) HOLLOW FIBER MEMBRANE-TYPE ARTIFICIAL LUNG

(75) Inventor: Tomokazu Niitsuma, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 583 days.

(21) Appl. No.: 11/990,566

(22) PCT Filed: Oct. 20, 2006

(86) PCT No.: PCT/JP2006/320919
§ 371 (c)(1),
(2), (4) Date: Feb. 15, 2008

(87) PCT Pub. No.: WO2007/060799
PCT Pub. Date: May 31, 2007

(65) Prior Publication Data
US 2009/0180924 A1    Jul. 16, 2009

(30) Foreign Application Priority Data

Nov. 24, 2005    (JP) ................................. 2005-338835

(51) Int. Cl.
*A61M 37/00*    (2006.01)
(52) U.S. Cl. .......................................... 604/6.16; 422/46
(58) Field of Classification Search .............. 422/45–48; 604/4.01, 5.01, 7, 19, 23, 317; 607/113
See application file for complete search history.

(56) References Cited

U.S. PATENT DOCUMENTS

| | | | |
|---|---|---|---|
| 5,312,589 A * | 5/1994 | Reeder et al. | .................. 422/45 |
| 5,429,184 A | 7/1995 | Bach et al. | |
| 2009/0018629 A1* | 1/2009 | Yoshida et al. | ............... 607/113 |

FOREIGN PATENT DOCUMENTS

| | | |
|---|---|---|
| CN | 2169428 Y | 6/1994 |
| EP | 1 715 279 A1 | 10/2006 |
| JP | 3-111057 A | 5/1991 |
| JP | 3-158167 | 7/1991 |

(Continued)

*Primary Examiner* — Tatyana Zalukaeva
*Assistant Examiner* — Benedict L Hanrahan
(74) *Attorney, Agent, or Firm* — Hamre, Schumann, Mueller & Larson, P.C.

(57) ABSTRACT

A hollow fiber bundle that is formed by arranging a plurality of porous hollow fiber membranes 8 in one direction; a heat exchange pipe bundle that is formed by arranging and laminating a plurality of heat exchange pipes 9 in one direction crossing the hollow fiber membranes and is apposed with the hollow fiber bundle; and a potting material 10 that is filled in a region including both end parts of the hollow fiber membranes and the heat exchange pipes and forms a blood channel extending across the hollow fiber membranes and the heat exchange pipes are provided. The housing includes: blood ports 3*a*, 3*b* that face both ends of the blood channel; gas headers 4*a*, 4*b* that form gas ports 5*a*, 5*b* facing both ends of the hollow fiber bundle; and heat exchange headers 6*a*, 6*b* that form heat exchange liquid ports 7*a*, 7*b* facing both ends of the heat exchange pipe bundle. The blood flows through the blood channel and an oxygen-containing gas flows through a bore of the hollow fiber membrane so as to perform the gas exchange, and the heat exchange liquid flows through a bore of the heat exchange pipe so as to perform the heat exchange. A hollow fiber membrane-type artificial lung, in which the heat exchange part is apposed with the gas exchange part without unnecessarily increasing a priming volume, can be structured.

6 Claims, 3 Drawing Sheets

FOREIGN PATENT DOCUMENTS

| | | |
|---|---|---|
| JP | 7-303695 A | 11/1995 |
| JP | 9-509351 | 9/1997 |
| JP | 11-206880 | 8/1999 |
| JP | 2004-160217 | 6/2004 |
| JP | 2005-224301 A | 8/2005 |
| WO | WO 2005/075922 A | 8/2005 |

* cited by examiner

HOLLOW FIBER MEMBRANE-TYPE ARTIFICIAL LUNG

TECHNICAL FIELD

The present invention relates to a hollow fiber membrane-type artificial lung that performs gas exchange by using a hollow fiber membrane, and particularly relates to a hollow fiber membrane-type artificial lung that is composed by laminating a heat exchange pipe bundle on a hollow fiber bundle so as to perform heat exchange as well as gas exchange.

BACKGROUND ART

It is known that an artificial lung in which blood can flow perpendicularly to a hollow fiber membrane can achieve gas exchange with high efficiency and a low pressure drop due to effective fracture of blood-side laminar film resistance, and has high efficiency in basic performance. Further, the artificial lung in which a heat exchange pipe bundle is laminated on a hollow fiber bundle performs heat exchange as well as gas exchange, thereby performing an operation for maintaining the temperature of blood in an appropriate range effectively. Such a hollow fiber membrane-type artificial lung described in Patent Document 1 or 2 will be described below with reference to FIG. 5.

The hollow fiber membrane-type artificial lung shown in FIG. 5 has a housing that includes a gas exchange part 21 and a heat exchange part 22 that are piled up. In bores of the gas exchange part 21 and a heat exchange part 22, a hollow fiber bundle that is a bundle of hollow fiber membranes 28, which are elements for the gas exchange, and a stainless pipe bundle that is a bundle of stainless pipes 29, which is an element for the heat exchange, are stored, respectively.

The hollow fiber bundle has a form in which a plurality of the porous hollow fiber membranes 28 are arranged and laminated such that an axial direction thereof is a horizontal direction. The stainless pipe bundle has a form in which a plurality of the stainless pipes 29 constituting heat exchange pipes are arranged and laminated such that an axial direction thereof is the horizontal direction. The stainless pipe 29 and the hollow fiber membrane 28 are arranged such that the directions of arranging the respective axes are parallel with each other.

In a circumferential region including both end parts of the hollow fiber membranes 28, a potting material is filled so as to form a potting part 30a. A bore of the potting part 30a forms a cylindrical blood channel that extends across the hollow fiber membranes 28 in a perpendicular direction. The potting material is filled also in a circumferential region including both end parts of the stainless pipes 29, thereby forming a potting part 30b. Also, a bore of the potting part 30b forms the cylindrical blood channel that extends across the stainless pipes 29 in the perpendicular direction.

In a boundary part between the gas exchange part 21 and the heat exchange part 22, outer shell walls of both parts are opened so as to form an opening gap part 33. The cylindrical blood channel that is formed by the potting part 30a of the hollow fiber bundle and the cylindrical blood channel that is formed by the potting part 30b of the stainless pipe bundle 29 are communicated with each other via the opening gap part 33, thereby forming the blood channel that is continuous in the perpendicular direction. On the outer shell walls of the heat exchange part 22 and the gas exchange part 21 that respectively correspond to an top end and a bottom end of the blood channel, a blood inlet port 23a and a blood outlet port 23b are provided.

At a left end part and a right end part of the gas exchange part 21, gas headers 24a, 24b for sealing the bores are provided, respectively. To the gas headers 24a, 24b, a gas inlet port 25a and a gas outlet port 25b are provided, respectively. Moreover, at a left end part and a right end part of the heat exchange part 22, cold/hot water headers 26a, 26b for sealing the bores are provided, respectively. To the cold/hot water headers 26a, 26b constituting the heat exchange headers, a cold/hot water inlet port 27a and a cold/hot water outlet port 27b for allowing cold water or hot water that is a heat exchange liquid to flow in and out are provided, respectively.

Blood that flows in from the blood inlet port 23a passes through the blood channel that is constituted of the bore of the potting part 30b, the opening gap part 33 and the bore of the potting part 30a, and flows out from the blood outlet port 23b.

Gaps 31a, 31b are formed near both ends of the hollow fiber bundle, by the gas headers 24a, 24b that respectively are provided on the left side and the right side of the gas exchange part 21, and the hollow fiber membrane 28 forming the hollow fiber bundle are opened to the gaps 31a, 31b on end faces of the potting part 30a. Thus, an oxygen-containing gas that flows in from the gas inlet port 25a fills in the gap 31a, enters the bore from one end of each follow fiber membrane 28, passes through the gap 31b from the other end of each follow fiber membrane 28, and then flows out from the gas outlet port 25b. During this time, the gas exchange is performed with the blood.

Moreover, gaps 32a, 32b are formed near both ends of the stainless pipe bundle 29, by the cold/hot water headers 26a, 26b that respectively are provided on a left side and a right side of the heat exchange part 22, and the stainless pipe constituting the stainless pipe bundle 29 is opened to the gaps 32a, 32b on end faces of the potting part 30b. Thus, the cold water or the hot water that flows in from the cold/hot water inlet port 27a fills in the gap 32a, enters the bore from one end of each stainless pipe, passes through the gap 32b from the other end of each stainless pile, and then flows out from the cold/hot water outlet port 27b. During this time, the heat exchange is performed with the blood.

Patent document 1: JP 11 (1999)-206880 A
Patent document 2: JP 9 (1997)-509351 A

DISCLOSURE OF INVENTION

Problem to be Solved by the Invention

In the hollow fiber membrane-type artificial lung with the above-described configuration, since the gas exchange part 21 and the heat exchange part 22 are laminated in parallel with each other, it is necessary to provide the gas headers 24a, 24b and the cold/hot water headers 26a, 26b at the boundary part between the gas exchange part 21 and the heat exchange part 22. This aims to separate an inflow and an outflow of gas and cold/hot water at both ends of the hollow fiber membrane 28 and the stainless pipe 29, respectively. In order to fit the gas headers 24a, 24b and the cold/hot water headers 26a, 26b to each other, a predetermined space is necessary between the hollow fiber bundle and the stainless pipe bundle in the perpendicular direction. That is, since the hollow fiber bundle and the stainless pipe bundle are arranged in parallel with each other, and the end parts thereof are close to each other, the gas headers 24a, 24b and the cold/hot water headers 26a, 26b are arranged closely to each other, and thus, even if the gas headers 24a, 24b and the cold/hot water headers 26a, 26b are arranged most closely to each other, a space that corresponds to a thickness of the outer shell wall is necessary between the hollow fiber bundle and the stainless pipe bundle at the boundary part thereof.

As a result, a region in which neither the hollow fiber membrane 28 nor the stainless pipe 29 is present, such as the opening gap part 33, is formed at the boundary therebetween. Since the blood passes also through this region, this region is a dead space that contributes to neither the gas exchange nor the heat exchange. Due to this dead space, a priming volume is increased unnecessarily.

The present invention aims to provide a hollow fiber membrane-type artificial lung in which a heat exchange part is apposed with the gas exchange part without increasing a priming volume unnecessarily, and a gas exchange rate and a heat exchange rate are improved.

Means for Solving Problem

The hollow fiber membrane-type artificial lung of the present invention includes: a hollow fiber bundle that is formed by arranging and laminating a plurality of porous hollow fiber membranes in one direction; a heat exchange pipe bundle that is formed by arranging and laminating a plurality of heat exchange pipes in one direction, and is apposed with the hollow fiber bundle; a potting material that is filled in a region including both end parts of the hollow fiber membrane and the heat exchange pipe bundle, and forms a blood channel extending across the hollow fiber membrane and the heat exchange pipe; and a housing including gas headers that store the hollow fiber bundle and the heat exchange pipe bundle and form a gas inlet port and a gas outlet port facing both ends of the hollow fiber membrane, respectively, heat exchange headers that face both ends of the heat exchange pipe bundle and form a heat exchange liquid inlet port and a heat exchange liquid outlet port respectively, and a blood inlet port and a blood outlet port facing both ends of the blood channel, and is configured such that a blood flows through the blood channel and a gas containing oxygen flows through a bore of the hollow fiber membrane so as to perform gas exchange between the blood and the gas, and a heat exchange liquid flows through a bore of the heat exchange pipe so as to perform heat exchange between the blood and the heat exchange liquid.

In order to solve the above-described problem, the hollow fiber membrane-type artificial lung of the present invention is characterized in that a direction of arranging the heat exchange pipes that constitute the heat exchange pipe bundle crosses a direction of arranging the hollow fiber membranes that constitute the hollow fiber bundle so as to laminate the hollow fiber bundle and the heat exchange pipe bundle closely to each other.

Effects of the Invention

According to the hollow fiber membrane-type artificial lung with the above-described configuration, since the hollow fiber bundle and the stainless pipe bundle are arranged so as to cross each other, the gas headers and the heat exchange headers that are arranged at both end parts thereof are not adjacent to each other. Thus, the gas headers and the heat exchange headers can be installed without providing a space between the hollow fiber bundle and the stainless pipe bundle. As a result, a dead space is not generated between the hollow fiber bundle and the stainless pipe bundle, and an unnecessary increase of the priming volume can be avoided. Further, due to a decrease of a dead volume, the heat exchange rate and the gas exchange rate can be improved.

EXPLANATION OF REFERENCE CODES

Figure 1:
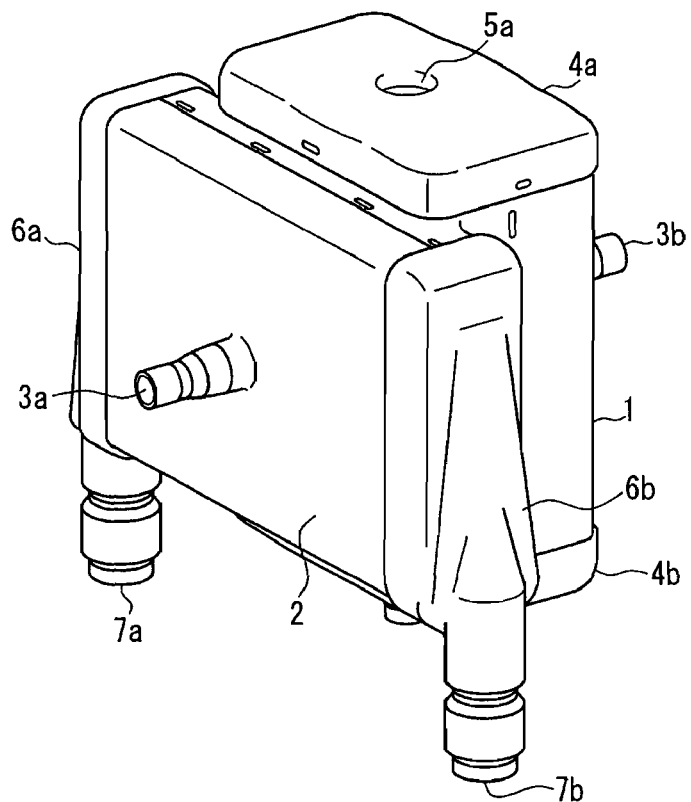
FIG. 1 is a perspective view showing an external appearance of a hollow fiber membrane-type artificial lung according to one embodiment of the present invention.

| | |
|---|---|
| 1, 21 | gas exchange part |
| 2, 22 | heat exchange part |
| 3a, 23a | blood inlet port |
| 3b, 23b | blood outlet port |
| 4a, 4b, 24a, 24b | gas header |
| 5a, 25a | gas inlet port |
| 5b, 25b | gas outlet port |
| 6a, 6b, 26a, 26b | cold/hot water header |
| 7a, 27a | cold/hot water inlet port |
| 7b, 27b | cold/hot water outlet port |
| 8, 28 | hollow fiber membrane |
| 9, 29 | stainless pipe |
| 10, 30a, 30b | potting part |
| 11a, 11b | gap |
| 12a, 12b | gap |
| 31a, 31b | gap |
| 32a, 32b | gap |
| 33 | opening gap part |

DESCRIPTION OF THE INVENTION

In the hollow fiber membrane-type artificial lung of the present invention with the above-described configuration, it is preferable that the direction of arranging the heat exchange pipes that constitute the heat exchange pipe bundle is perpendicular to the direction of arranging the hollow fiber membranes that constitute the hollow fiber bundle.

Moreover, it is preferable that the heat exchange liquid inlet port and the heat exchange liquid outlet port that are formed by the heat exchange headers are formed in the same direction as a direction of the gas outlet port. The reason for this will be described below.

By providing the gas outlet port so as to be directed downwardly, even when water drops caused by condensation are generated in the bore of the hollow fiber membrane, the bore of the hollow fiber membrane can be prevented from being blocked by the water drops. Since a flowing direction of the gas is the same as a falling direction of the water drops, the water drops caused by the condensation is likely to be moved and removed. Whereas, by providing the heat exchange liquid inlet port and the heat exchange liquid outlet port in a downward direction similarly to the gas outlet port, it becomes easier to dispose piping of the heat exchange liquid, such as the cold/hot water, only at a lower position of the hollow fiber membrane-type artificial lung without routing at a higher position thereof, and contamination caused in the case of connecting a line of the heat exchange water with each outlet port or in the case of leakage of the heat exchange liquid can be prevented. By providing the hollow fiber bundle and the stainless pipe perpendicularly to each other, the gas outlet port and the heat exchange liquid port can be disposed appropriately as described above.

Moreover, the heat exchange pipe can be a stainless pipe.

Moreover, it is preferable that a cross section of the blood channel in a flowing direction of the blood is substantially circular. By making the blood channel to have a circular cross-section, a blood dogging part is not likely to be generated, and formation of a thrombus is reduced. Moreover, the hollow fiber membrane-type artificial lung that provides the most appropriate flow of the blood, decreases a priming volume, and can decrease a size thereof sufficiently with respect to the obtained gas exchange capability can be realized. Further, by making the channel to have the circular cross-section, a potting step is easier.

Moreover, it is preferable that a blood channel formed by the potting material crossing the hollow fiber bundle and a blood channel formed by the potting material crossing the hollow fiber bundle are adjusted to be flush with each other without forming a step difference at a boundary between the blood channels. Thereby, the flow of the blood can be smoothed, and occurrence of a thrombus and stagnation caused by a disruption of a blood flow can be reduced.

The hollow fiber membrane-type artificial lung according to one embodiment of the present invention will be described specifically below with reference to drawings.

FIG. 1 is a perspective view showing an external appearance of the hollow fiber membrane-type artificial lung according to the present embodiment. Composing elements for gas exchange and heat exchange are stored in a housing that is composed of a gas exchange part 1 and a heat exchange part 2. As described below, in the bore that is formed by the gas exchange part 1 and the heat exchange part 2, the blood channel 13, 14 is formed so as to penetrate the gas exchange part 1 and the heat exchange part 2 in a horizontal direction, and a blood inlet port 3a and a blood outlet port 3b are provided on outer shell walls of the heat exchange part 2 and the gas exchange part 1 that correspond to both ends of the blood channel 13, 14, respectively.

At a top end part and a bottom end part of the gas exchange part 1, gas headers 4a, 4b for sealing the bores are provided, respectively. At the gas headers 4a, 4b, a gas inlet port 5a and a gas outlet port 5b (see FIG. 2) are provided, respectively. At a left end part and a right end part of the heat exchange part 2, cold/hot water headers 6a, 6b for sealing the bores are provided, respectively. At bottom end parts of the cold/hot water headers 6a, 6b that constitute the heat exchange headers, a cold/hot water inlet port 7a and a cold/hot water outlet port 7b that allows cold water or hot water as a heat exchange liquid to flow in and out are provided, respectively. That is, the cold/hot water inlet port 7a and the cold/hot water outlet port 7b have the same directions as the direction of the gas outlet port 5b.

Figure 2:
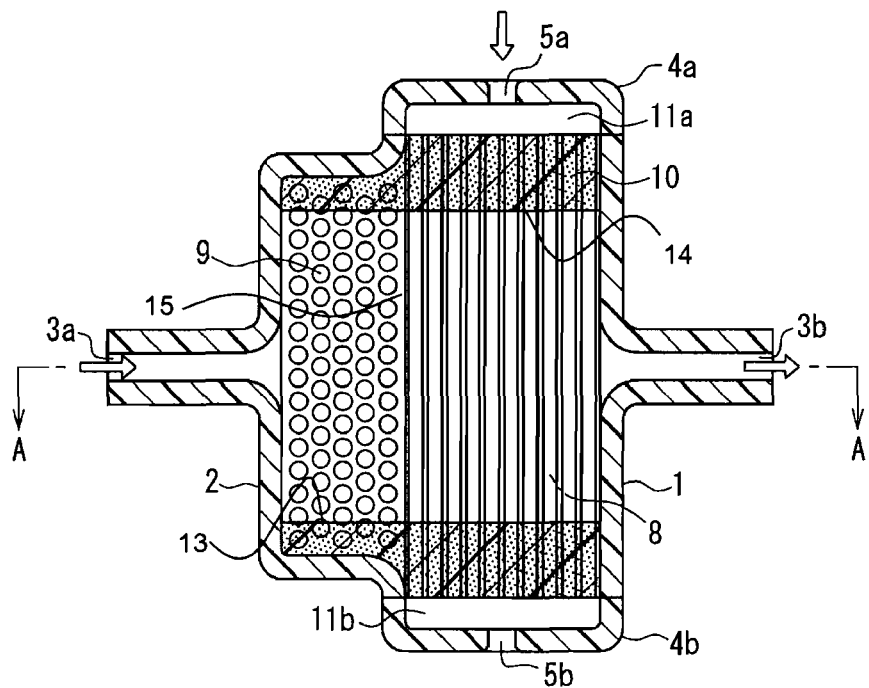
FIG. 2 is a cross-sectional view showing an internal configuration of the hollow fiber membrane-type artificial lung.

FIG. 2 is a cross-sectional view including the blood inlet port 3a and the blood outlet port 6b of FIG. 1 in the perpendicular direction. As shown in FIG. 2, a hollow fiber bundle that is a bundle of hollow fiber membranes 8 is disposed in the bore of the gas exchange part 1. The hollow fiber bundle has a form in which a plurality of the porous hollow fiber membranes 8 are arranged and laminated such that an axial direction thereof is the perpendicular direction. In the bore of the heat exchange part 2, a stainless pipe bundle is disposed. The stainless pipe bundle has a form in which a plurality of stainless pipes 9 that constitute the heat exchange pipes are arranged and laminated such that an axial direction thereof is a horizontal direction. Thus, the direction of arranging the stainless pipes 9 that form the stainless pipe bundle is perpendicular to the direction of arranging the hollow fiber membranes 8 that form the hollow fiber bundle. The hollow fiber bundle and the stainless pipe bundle are arranged closely to each other at a boundary portion 15 therebetween. A space between the hollow fiber bundle and the stainless pipe bundle ranges from 0 mm to 2 mm.

Figure 3:
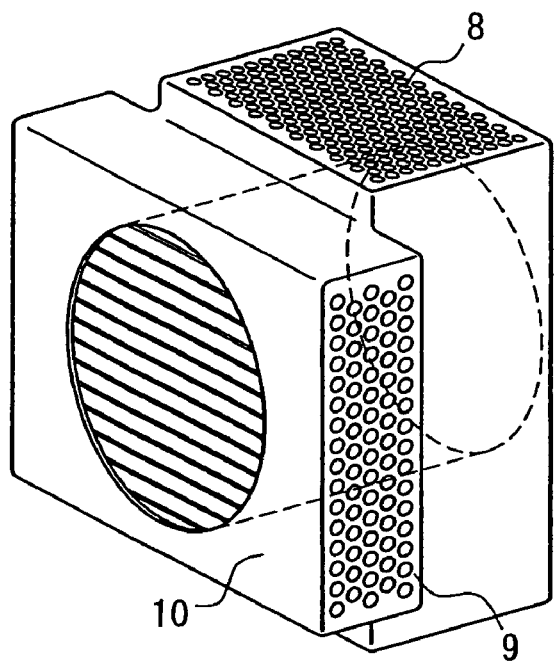
FIG. 3 is a perspective view showing a hollow fiber-type gas exchange part and heat exchange part of the hollow fiber membrane-type artificial lung.

In a circumferential region including both end parts of the hollow fiber bundle and the stainless pipe bundle, a potting material is filled so as to form a potting part 10. A bore of the potting part 10 forms a cylindrical blood channel 13, 14 that extends across the hollow fiber membranes 8 and the stainless pipes 9 in the horizontal direction. In FIG. 3, only the hollow fiber membranes 8, the stainless pipes 9 and the potting part 10 that is formed at a circumferential part thereof are taken to be shown, for easier recognition of the form of the blood channel 13, 14 formed by the potting part 10.

As shown by arrows in FIG. 2, blood that flows in from the blood inlet port 3a passes through the blood channel 13, 14 of the bore of the potting part, and flows out from the blood outlet port 3b. Moreover, gaps 11a, 11b are formed near both ends of the hollow fiber membranes 8 that form the hollow fiber bundle, by the gas headers 4a, 4b that are provided on an upper side and a lower side of the gas exchange part 1. And, the hollow fiber membranes 8 are opened to the gaps 11a, 11b on end faces of the potting part 10. Thus, an oxygen-containing gas that flows in from the gas inlet port 5a fills in the gap 11a, enters the bore from one end of each hollow fiber membrane 8, passes through the gap 11b from the other end of each hollow fiber membrane 8, and flows out from the gas outlet port 5b. During this time, gas exchange is performed with the blood.

Figure 4:
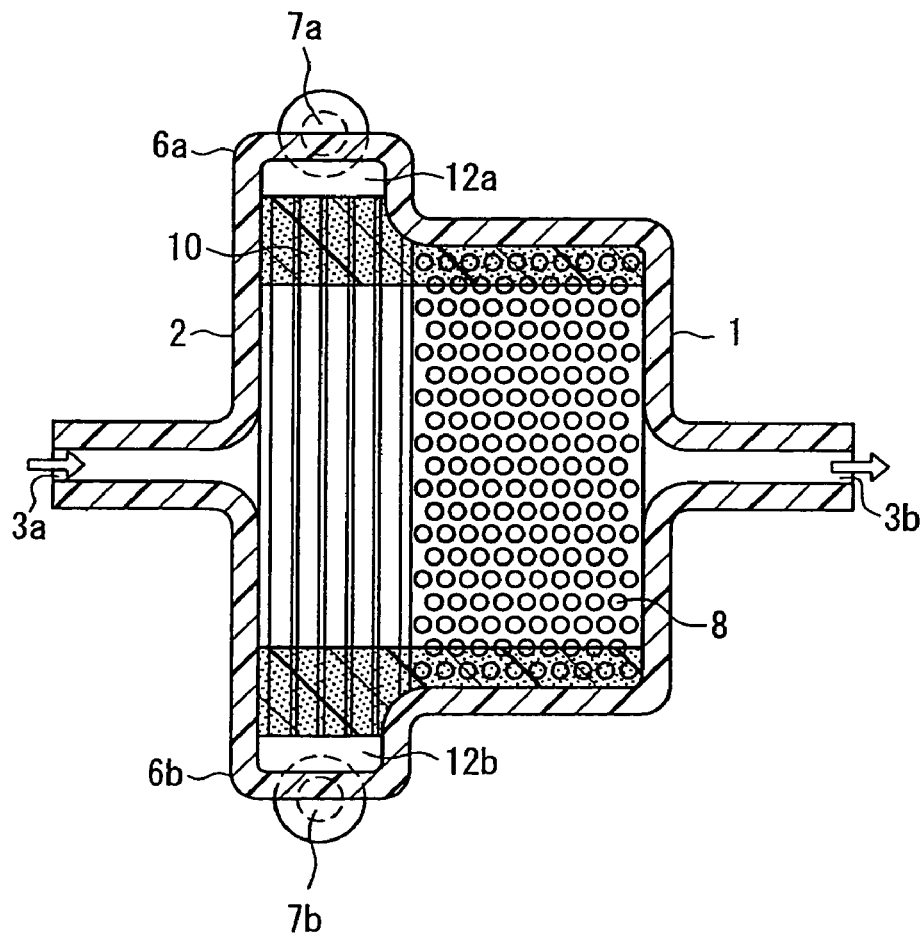
FIG. 4 is a cross-sectional view taken on line A-A of FIG. 2.

FIG. 4 is a cross-sectional view taken on line A-A of FIG. 2. As shown in the figure, gaps 12a, 12b are formed near both ends of the stainless pipes 9 that form the stainless pipe bundle by the cold/hot water headers 6a, 6b that are provided on a left side and a right side of the heat exchange part 2, and the stainless pipes 9 are opened to the gaps 12a, 12b on the end faces of the potting part 10. Thus, cold water or hot water as the heat exchange liquid that flows in from the cold/hot water inflow port 7a fills in the gap 12a, enters the bore from one end of each stainless pipe 9, passes through the gap 12b from the other end of each stainless pipe 9, and flows out from the cold/hot water outlet port 7b. During this time, heat exchange is performed with the blood.

Figure 5:
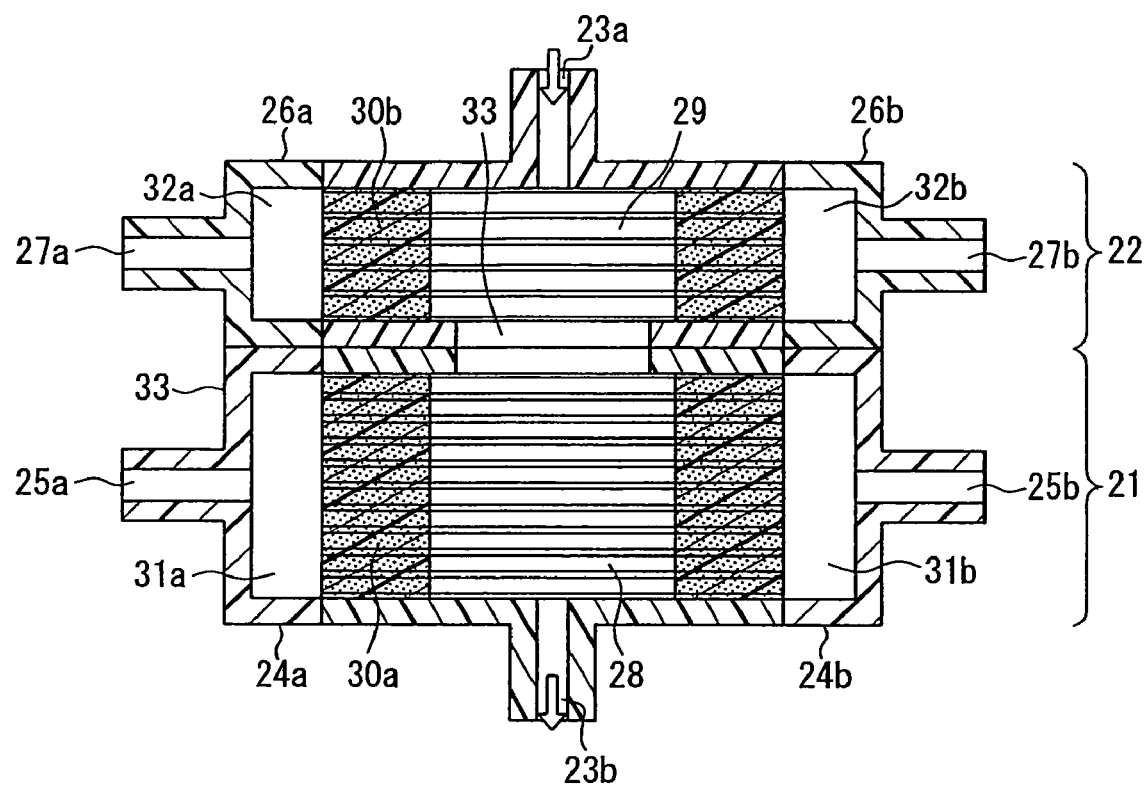
FIG. 5 is a cross-sectional view showing a configuration of a hollow fiber membrane-type artificial lung in a conventional example.

In the hollow fiber membrane-type artificial lung with the above-described configuration, the hollow fiber bundle and the stainless pipe bundle are arranged closely to each other, and the opening gap part 33 that is a dead space as suggested in the conventional example of FIG. 5 is not necessary. The reason for this is because, since the hollow fiber membrane 8 and the stainless pipe 9 are arranged perpendicularly to each other, the gas headers 4a, 4b and the cold/hot water headers 6a, 6b, which are disposed on both ends of the hollow fiber membrane 8 and the stainless pipe 9, are positioned separately so as not to be adjacent to each other. Thus, the gas headers 4a, 4b and the cold/hot water headers 6a, 6b can be installed without providing a space between the hollow fiber bundle and the stainless pipe bundle. As a result, an unnecessary increase of the priming volume can be avoided. The priming volume is a volume of the blood that is filled in modules of the gas exchange part 1 and the heat exchange part 2 during an operation of the artificial lung, and as the priming volume is smaller, a burden on the patient is smaller, thereby being more advantageous in practical use.

Moreover, it not necessary that the hollow fiber membrane 8 and the stainless pipe 9 are perpendicular to each other exactly. That is, if they cross each other, an equivalent effect can be obtained.

A specific effect obtained by arranging the hollow fiber membrane 8 and the stainless pipe 9 perpendicularly and forming the cold/hot water inlet port 7a and the cold/hot water outlet port 7b in the same direction as the gas outlet port 5b will be described below.

Firstly, by directing the gas outlet port 5b downwardly, the inconvenience caused by condensation can be prevented. That is, the gas flowing through the hollow fiber membrane 8 loses its temperature due to the influence of the blood, whereby condensation may be caused. As a result, the bore of the hollow fiber membrane 8 is blocked by water drops, and the flow of the gas deteriorates, thereby decreasing an efficiency the gas exchange. Even in such a situation, when directing the gas outlet port 5b downwardly, the water drops flow out downward. Further, since the direction of the movement of the water drops is the same as the direction of the flow of the gas, the water drops are likely to be removed, and the bore of the hollow fiber membrane 8 is prevented from being blocked by the water drops.

Whereas, it also is advantageous to direct the cold/hot water inlet port 7a and the cold/hot water outlet port 7b downwardly. This aims to dispose piping of the cold/hot water only at a lower position of the hollow fiber membrane-type artificial lung without routing at a higher position thereof. Since the cold/hot water for the heat exchange is not necessarily maintained hygienically, it is not desirable to locate the piping of the cold/hot water at the higher position of the hollow fiber membrane-type artificial lung, considering the influence of the contamination in the case of leakage of the cold/hot water. If directing the cold/hot water inlet port 7a and the cold/hot water outlet port 7b downwardly, the routing of the piping at the higher position of the hollow fiber membrane-type artificial lung can be avoided, by the reasonable and natural piping.

In order to direct the cold/hot water inlet port 7a and the cold/hot water outlet port 7b downwardly, it is advantageous to arrange the stainless pipes 9 in the horizontal direction. If arranging the stainless pipes 9 in the vertical direction, the piping in the downward direction from the port that corresponds to a top end of the stainless pipe 9 is slightly unreasonable. Moreover, if directing the stainless pipes 9 vertically, the piping is routed once at the higher position of the hollow fiber membrane-type artificial lung, which is not preferable.

For the reasons described above, it is advantageous for the piping in the practical use to arrange the hollow fiber membrane 8 and the stainless pipe 9 perpendicularly to each other.

Moreover, by making the blood channel that is formed by the potting part 10 to have the circular cross section as described above, a blood clogging part is not likely to be generated, and the formation of a thrombus is decreased. Moreover, the hollow fiber membrane-type artificial lung, in which the flow of the blood is most appropriate, the priming volume is decreased, and whose size can be decreased sufficiently with respect to the obtained gas exchange capability, can be realized.

Further, by making the channel to have the circular cross section, the potting step is easier. For filling the potting material into the end parts of the hollow fiber bundle and the stainless pipe bundle, the hollow fiber bundle and the stainless pipe bundle are placed in the housing, and thereafter, the potting material is filled centrifugally. That is, while rotating the hollow fiber bundle and the stainless pipe bundle around an axis to be a center of the blood channel within a plane that is parallel with the hollow fiber membranes 8 of the hollow fiber bundle and the stainless pipes 9 of the stainless pipe bundle and is perpendicular to the direction of the blood channel, the potting material is filled. Thereby, the potting material is filled so as to form the bore having the circular cross section. According to this method, the channel having a substantially circular cross section can be formed easily. Moreover, in one step for filling the potting material, all sides of the hollow fiber bundle and the stainless pipe bundle can be fixed, thus simplifying the manufacturing steps significantly. Further, since no step difference is present in the blood channel, occurrence of blood clogging and formation of a thrombus can be suppressed.

In the hollow fiber membrane-type artificial lung with the above-described configuration, as a material of the housing including the gas exchange part 1, the gas headers 4a, 4b, the heat exchange part 2 and the cold/hot water headers 6a, 6b, for example, polycarbonate can be used. As a material of the hollow fiber membrane, a urethane resin can be used. The potting material preferably has a double-layered structure in which an outer side is made of an epoxy resin and an inner side is made of a urethane resin. The material of the outer side of the potting material is selected for improving cohesion with an inner surface of the housing, and the material of the inner side thereof is selected for improving cohesion with the hollow fiber membranes and the stainless pipes.

INDUSTRIAL APPLICABILITY

According to the hollow fiber membrane-type artificial lung of the present invention, the heat exchange part can be provided with the gas exchange part without unnecessarily increasing the priming volume, and it is usefully applied to a hollow fiber membrane-type artificial lung that is configured to perform the heat exchange as well as the gas exchange.

The invention claimed is:

1. A hollow fiber membrane-type artificial lung comprising:
   a hollow fiber bundle that is formed by arranging and laminating a plurality of porous hollow fiber membranes in one direction;
   a heat exchange pipe bundle that is formed by arranging and laminating a plurality of heat exchange pipes in one direction, and is apposed with the hollow fiber bundle;
   a potting material that is filled in a region including both end parts of the hollow fiber membrane and the heat exchange pipe bundle, and forms a blood channel extending across the hollow fiber membrane bundle and the heat exchange pipe bundle; and
   a housing for containing the hollow fiber bundle and the heat exchange pipe bundle, comprising
   gas headers that form a gas inlet port and a gas outlet port facing both ends of the hollow fiber membrane, respectively,
   heat exchange headers that form a heat exchange liquid inlet port and a heat exchange liquid outlet port facing both ends of the heat exchange pipe bundle, respectively, and
   a blood inlet port and a blood outlet port facing both ends of the blood channel,
   the hollow fiber membrane-type artificial lung being configured such that a blood flows through the blood channel and a gas containing oxygen flows through a bore of the hollow fiber membrane so as to perform gas exchange between the blood and the gas, and a heat exchange liquid flows through a bore of the heat exchange pipe so as to perform heat exchange between the blood and the heat exchange liquid, wherein the housing includes a single region for a gas exchange part provided with the hollow fiber bundle and a single region for a heat exchange part provided with the heat exchange pipe bundle, the hollow fiber bundle of the single region for the gas exchange part being disposed adjacent to the heat exchange pipe bundle of the single region for the heat exchange part at a boundary within the blood channel between the single region for the heat exchange part and the single region for the gas exchange part, all of the hollow fiber membranes forming the hollow fiber bundle and all of the heat exchange pipes forming the heat exchange pipe bundle such that blood passing from the blood inlet port to the blood outlet port passes through one of the hollow fiber bundle in the single region for the gas exchange part or the heat exchange bundle in the single region of the heat exchange part prior to passing through the other of the heat exchange bundle in the single region of the heat exchange part or the hollow fiber bundle in the single region for the gas exchange part, a longitudinal direction of the heat exchange pipes constituting the heat exchange pipe bundle crosses a longitudinal direction of the hollow fiber membranes constituting the hollow fiber bundle.

2. The hollow fiber membrane-type artificial lung according to claim 1, wherein the direction of arranging the heat exchange pipes constituting the heat exchange pipe bundle is perpendicular to the direction of arranging the hollow fiber membranes constituting the hollow fiber bundle.

3. The hollow fiber membrane-type artificial lung according to claim 1, wherein the heat exchange liquid inlet port and the heat exchange liquid outlet port that are formed by the heat exchange headers are arranged such that the heat exchange liquid inlet port and the heat exchange liquid outlet are arranged on a first side of the hollow fiber membrane-type artificial lung and extend along a same direction as a direction extending from the gas inlet port to the gas outlet port.

4. The hollow fiber membrane-type artificial lung according to claim 1, wherein the heat exchange pipe is a stainless pipe.

5. The hollow fiber membrane-type artificial lung according to claim 1, wherein a cross section of the blood channel in a flowing direction of the blood is substantially circular.

6. The hollow fiber membrane-type artificial lung according to claim 1, wherein a blood channel formed by the potting material crossing the hollow fiber bundle and a blood channel formed by the potting material crossing the heat exchange pipe bundle are adjusted to be flush with each other without forming a step difference at a boundary between the blood channels.

* * * * *